(12) United States Patent
Yu et al.

(10) Patent No.: US 6,593,092 B2
(45) Date of Patent: Jul. 15, 2003

(54) BETA 2 ADRENERGIC POLYMORPHISM DETECTION

(75) Inventors: Hong Yu, Long Grove, IL (US); Barbara T. Merchant, Wilmette, IL (US)

(73) Assignee: Abbott Laboratories, Abbott Park, IL (US)

( * ) Notice: Subject to any disclaimer, the term of this patent is extended or adjusted under 35 U.S.C. 154(b) by 54 days.

(21) Appl. No.: 09/973,132

(22) Filed: Oct. 9, 2001

(65) Prior Publication Data

US 2002/0137069 A1 Sep. 26, 2002

Related U.S. Application Data

(63) Continuation-in-part of application No. 09/542,718, filed on Apr. 4, 2000, now abandoned.

(51) Int. Cl.[7] .......................... C12Q 1/68; C12P 19/34; C07H 21/04
(52) U.S. Cl. .......................... 435/6; 435/91.2; 435/810; 536/23.5; 536/24.31; 536/24.33
(58) Field of Search .......................... 435/6, 91.2, 810; 536/23.5, 24.31, 24.33

(56) References Cited

U.S. PATENT DOCUMENTS

| | | |
|---|---|---|
| 4,948,882 A | 8/1990 | Ruth |
| 5,142,047 A | 8/1992 | Summerton et al. |
| 5,185,444 A | 2/1993 | Summerton et al. |
| 5,210,015 A | 5/1993 | Gelfand et al. |
| 5,310,652 A | 5/1994 | Gelfand et al. |
| 5,322,770 A | 6/1994 | Gelfand |
| 5,424,414 A | 6/1995 | Mattingly |
| 5,464,746 A | 11/1995 | Fino |
| 5,679,635 A | 10/1997 | Matalon et al. |
| 5,925,517 A | 7/1999 | Tyagi et al. |

FOREIGN PATENT DOCUMENTS

| | | |
|---|---|---|
| WO | 9220702 | 11/1992 |
| WO | 9839477 | 9/1998 |

OTHER PUBLICATIONS

Tyagi, S. and Kramer, F.R. Molecular beacons: probes that fluoresce upon hybridization. Nature Biotechnology 14:303–308. [Mar. 1996]).*

Dewar, J.C., et al. The glutamine 27 $\beta_2$–adrenoceptor polymorphism is associated with elevated 1gE levels in asthmatic families, Journal of Allergy and Clinical Immunology, United Kingdom, 100(2), pp. 261–265 (1997).

Drazen, J.M., et al., "$\beta_2$ adrenoceptor polymorphisms" Thorax, USA, 51, pp. 1168 (1996).

Liggett, S.B., "Polymorphism of the $\beta_2$–Adrenergic Receptor and Asthma" American Journal of Respiratory and Critical Care Medicine, USA 156:S, pp. 156–162 (1997).

Martinez, F.D., et al., "Association between Genetic Polymorphisms of the $\beta_2$–Adrenoceptor and Response to Albuterol in Children with and without a History of Wheezing", Journal of Clinical Investigation., USA 100, pp. 3184–3188 (1997).

* cited by examiner

Primary Examiner—Carla J. Myers
Assistant Examiner—Diana Johannsen
(74) Attorney, Agent, or Firm—David J. Schodin

(57) ABSTRACT

Nucleic acid sequences are provided that are useful as amplification primers, hybridization probes, and as a portion of molecular beacon probes for amplifying and detecting polymorphisms of the β2 adrenergic receptor gene, compositions and kits incorporating the same, and methods employing the same.

7 Claims, No Drawings

BETA 2 ADRENERGIC POLYMORPHISM DETECTION

RELATED APPLICATION

This application is a continuation-in-part of U.S. patent application Ser. No. 09/542,718, filed Apr. 4, 2000.

TECHNICAL FIELD

The present invention relates to nucleic acid polymorphisms and, in particular, relates to detecting a single nucleotide polymorphism using nucleic acid amplification technology.

BACKGROUND OF THE INVENTION

Studies designed to determine the sequence of the human genome, as well as studies designed to compare human genomic sequences, have elicited information regarding polymorphisms in the human genome. A wide variety of polymorphisms in the human genome have previously been described. The various types of human genetic polymorphisms include single base substitutions; insertions or deletions; variable numbers of tandem repeats; deletions of all or a large part of a gene; gene amplifications; and chromosomal rearrangements. Generally, polymorphisms that involve a single nucleotide are called single nucleotide polymorphisms ("SNPs").

Recently, a SNP in codon 16 of the β2 adrenergic receptor gene has been reported and associated with a variation in response to β agonist therapy (Drazen, J M et al, Thorzx, 1996, 51:1168; Liggett, S. B., Am. J. Respir. Crit. Care Med., 1997, 156:S156–62; Martinez, F. D. et al, J. Clin. Invest., 1997, 100:3184–8). Adrenergic receptors are hormone receptors on the surfaces of various cells. When bound to an adrenergic receptor site, a hormone can trigger a cascade of cellular events. Hence, adrenergic receptors and the hormones that bind to them, in large part form the mechanism that controls cellular events at a molecular level. Many pharmacological compounds mimic molecules that bind to adrenergic receptor sites and, in this manner, clinically regulate cellular function. For example, a class of drugs known as beta-agonists bind to β2 adrenergic receptor sites and are widely used as a medication for asthma. Individuals with a SNP in codon 16 of the β2 adrenergic gene, however, may not respond to such therapies due to a conformational, or other, change in the receptor that causes a decrease in the affinity between the receptor and the medication or hormone.

It would be advantageous, therefore, to provide a means for detecting the polymorphism in codon 16 of the β2 adrenergic receptor gene prior to prescribing medications that would not be efficacious as a result of the polymorphism.

SUMMARY OF THE INVENTION

Provided herein are methods capable of analyzing polymorphic nucleic acid sequences in a manner suitable for automation. The present invention provides reagents, methods, and kits for amplifying and detecting a target sequence having a polymorphism at codon 16 of the β2 adrenergic receptor gene in a test sample. In particular, SEQ ID NO: 2 and SEQ ID NO: 3 can be employed as amplification primers to amplify the target sequence designated herein as SEQ ID NO: 1. It was discovered that these primers specifically and sensitively produce an amplification product that is amenable to detection with SEQ ID NOs: 4, 5, and with molecular beacon probes comprising SEQ ID NOs: 6, 7, 8, and 9. SEQ ID NO: 4 is an internal hybridization probe specific for the wild-type sequence and SEQ ID NO: 5 is an internal hybridization probe specific for the variant (polymorphic) sequence. Similarly, SEQ ID NOs: 6 and 7 are the nucleotide sequence incorporable into a molecular beacon probe for the wild-type sequence, while SEQ ID NOs: 8 and 9 are nucleotide sequences incorporable into molecular beacon probes selective for the variant (polymorphic) sequences.

The target sequence, designated herein as SEQ ID NO: 1, can be amplified by forming a reaction mixture comprising nucleic acid amplification reagents, a test sample containing a target sequence, and primers designated SEQ ID NOs. 2 and 3. Following amplification, the amplified target sequence can be detected. For example, the probes designated SEQ ID NOs: 4 and 5, or the molecular beacon probes incorporating the sequences designated SEQ ID NOs: 6, 7, 8 and 9, can be employed to hybridize to the amplified target sequence to form a probe/amplification product hybrid, which can be detected using any suitable technique selected from a variety of well known techniques. Hence, detecting a probe/amplification product hybrid wherein the probe is SEQ ID NO: 4 indicates the presence of the wild-type sequence. On the other hand, detecting of a probe/amplification product hybrid wherein the probe is SEQ ID NO: 5 would indicate the presence of the polymorphic sequence. Similarly, detecting a signal indicative of the target-bound state from the molecular beacon probe comprising the nucleotide sequence designated SEQ ID NO: 6 or SEQ ID NO: 7 in the presence of the amplification product indicates the presence of the wild-type sequence, whereas detecting a signal indicative of the target-bound state from one of the molecular beacon probes comprising the nucleotide sequence designated SEQ ID NO: 8 or SEQ ID NO: 9 in the presence of the amplification product indicates the presence of the variant (polymorphic) sequence.

DETAILED DESCRIPTION OF THE INVENTION

The present invention provides reagents, methods, and kits for amplifying and detecting a target sequence in a test sample. In particular, SEQ ID NO: 2 and SEQ ID NO: 3 can be employed as amplification primers to amplify a nucleic acid sequence potentially comprising the polymorphism in codon 16 of the β2 adrenergic receptor gene. Hence, both the wild-type and polymorphic version of the target sequence can be amplified using SEQ ID NOs:2 and 3. The sequence AACGGCAGCG CCTTCTTGCT GGCACCCAAT AGAAGCCATG CGCCGGACCA CGACGTCACG CAGCAAAGGG ACGAGGTGTG GGTGGTGGGC ATGGGCATCG TCATGT (SEQ ID NO: 1) is presented as a representative target sequence. Probe sequences, having SEQ ID NO: 4 or SEQ ID NO: 5 can be employed to detect or distinguish the amplification product produced by primers designated SEQ ID NO: 2 and SEQ ID NO: 3 (e.g., indicate the presence of the wild-type or polymorphic sequence in the test sample). Similarly, molecular beacon probes incorporating the nucleotide sequences designated SEQ ID NOs: 6, 7, 8, and 9 can be employed to detect and/or distinguish the amplification product produced by primers designated SEQ ID NOs: 2 and 3 (e.g., indicate the presence of the wild-type or polymorphic sequence in the test sample).

Nucleotide sequences useful in the context of the present invention include:

```
SEQ ID NO: 2:  aacggcagcg ccttcttgc

SEQ ID NO: 3:  acatgacgat gcccatgcc

SEQ ID NO: 4:  caatagaagc catgc

SEQ ID NO: 5:  cccaatggaa gcc

SEQ ID NO: 6:  cgtccgcacc caatagaagc catcggacg,

SEQ ID NO: 7:  cgtccgatgg cttctattgg gtgcggacg,

SEQ ID NO: 8:  cgtccgcacc caatggaagc catcggacg, and

SEQ ID NO: 9:  cgtccgatgg cttccattgg gtgcggacg,
``` as well as artificial analog sequences wherein one or more of the naturally-occurring nucleotides identified above is replaced with a synthetic analog of the nucleotide. In three preferred embodiments, the molecular beacons comprising the nucleotide sequences designated SEQ ID NOs: 6, 7, 8, and 9 consist entirely or essentially of these nucleotide sequences, linked to fluorescein and dabcyl. Molecular beacon probes comprising the nucleotides sequences designated SEQ ID NO: 6 and SEQ ID NO: 9 are preferred to molecular beacon probes comprising SEQ ID NO: 7 and SEQ ID NO: 8, respectively.

The primer, probe, and nucleotide sequences of the molecular beacons disclosed herein, can comprise deoxyribonucleic acid (DNA), ribonucleic acid (RNA) or nucleic acid analogs, such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference, as well as other nucleic acid analogs known in the art. For example, the skilled artisan will recognize that where the oligonucleotide designated as T (i.e., thymidine) is indicated, this oligonucleotide also designates U in embodiments where RNA is employed rather than DNA, and designates a nucleic acid analog where non-naturally occurring nucleotide residues are incorporated into the sequences of the present invention. (Such sequences routinely can be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. Pat. Nos. 5,464,746; 5,424,414; and 4,948,882, each of which are herein incorporated by reference in their entirety. In certain embodiments, the probes and molecular beacon probes of the present invention preferably contain only the naturally-occurring RNA nucleotides (i.e., A, G, C, and U), and more preferably, contain only the naturally-occurring DNA nucleotides (i.e., A, G, C, and T). Sequences employed as primers preferably have DNA at the 3' end of the sequence, and more preferably, are completely comprised of DNA.

A "target sequence" is a nucleic acid sequence that is both amplified and detected, or comprises a nucleotide sequence complementary to SEQ ID NO: 1. While the term target sequence is sometimes referred to as single stranded, the skilled artisan will recognize that the target sequence as used herein can be double stranded.

The term "test sample" as used herein, means anything suspected of containing the target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues such as heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like. Most typically, the test sample will be whole blood.

SEQ ID NOs: 2 and 3 can be used as amplification primers according to amplification procedures well known in the art to amplify the target sequence. Preferably, the sequences provided herein are employed according to the principles of the polymerase chain reaction (PCR) described in U.S. Pat. Nos. 4,683,195 and 4,683,202 which are herein incorporated by reference. It will be understood by those skilled in the art that in the event that the target sequence is RNA, a reverse transcription step can be included in the amplification of the target sequence. Enzymes having reverse transcriptase activity are well known for their ability to produce a DNA sequence from an RNA template. Reverse transcription PCR (RT PCR) is well known in the art and described in U.S. Pat. Nos. 5,310,652 and 5,322,770, which are herein incorporated by reference.

Thus, amplification methods of the present invention generally comprise the steps of forming a reaction mixture comprising nucleic acid amplification reagents, amplification primers (i.e., SEQ ID NO: 2 and SEQ ID NO: 3), and a test sample suspected of containing a target sequence. Upon formation of the reaction mixture, the so-formed reaction mixture is subjected to amplification conditions to generate at least one copy of the target sequence. It will be understood that subjecting the reaction mixture may be repeated several times such as by thermal cycling the reaction mixture as is well known in the art.

As stated above, the reaction mixture comprises "nucleic acid amplification reagents" that include reagents which are well known and may include, but are not limited to, an enzyme having polymerase activity (and, as necessary, reverse transcriptase activity), enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

"Amplification conditions" are defined generally as conditions which promote hybridizing or annealing of primer sequences to a target sequence and subsequent extension of the primer sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e., within 10° C.) the melt temperature. Ionic strength or "salt" concentration also impacts the melt temperature, since small cations tend to stabilize the formation of duplexes by interacting with the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art.

Amplification products produced as above can be detected during or subsequently to the amplification of the target sequence. Detection platforms that can be employed to detect the amplification products produced with SEQ ID NOs: 2 and 3 using probe sequences having SEQ ID NOs: 4 and 5 or molecular beacon probes comprising SEQ ID NOs: 6, 7, 8, and/or 9, include any of the well known homogeneous or heterogeneous techniques well known in the art. Examples of homogeneous detection platforms can include the use of Fluorescence Resonance Energy Transfer (FRET) labels attached to probes that emit a signal in the presence of the target sequence, such as, without limitation, fluorescein and dabcyl. So-called TaqMan assays described in U.S. Pat. No. 5,210,015 (herein incorporated by reference) and molecular beacon probes and assays described in U.S. Pat. No. 5,925,517 (herein incorporated by reference) are examples of techniques that can be employed to homogeneously detect nucleic acid sequences. Additionally, such platforms can be employed to detect the production of amplification product in a real-time manner. It will be understood that the probes can be modified to such that they are suitable for use according to the particular detection platform employed.

Gel electrophoresis, for example, can be employed to detect the products of an amplification reaction after its completion using molecular weight markers. However, amplification products can be detected heterogeneously using labeled probes and solid supports. Hence, methods for detecting the amplified target sequence can include the steps of (a) hybridizing at least one hybridization probe (e.g., SEQ ID NOs: 4 and 5) to the nucleic acid sequence complementary to the target sequence, so as to form a hybrid comprising the probe and the nucleic acid sequence complementary to the probe; and (b) detecting the hybrid as an indication of the presence of the target sequence in the test sample.

Hybrids formed as above can be detected using microparticles and labels that can be used to separate and detect such hybrids. Preferably, detection is performed according to the protocols used by the commercially available Abbott LCx® instrumentation (Abbott Laboratories; Abbott Park, Ill.).

Similarly, methods for detecting the amplified target sequence include the steps of (a) contacting a molecular beacon probe comprising a nucleic acid having the sequence designated SEQ ID NO: 6, 7, 8, or 9 with a target sequence or amplification product under suitable conditions, and (b) observing the emission spectrum or spectra of the molecular beacon to determine whether or how much of the target or amplification product is present.

Molecular beacon probes comprising SEQ ID NOs: 6, 7, 8, and/or 9 also can be used to detect the presence or quantity of the amplification product in other embodiments. For example, molecular beacon probes can be added to the amplification reaction, thereby allowing essentially simultaneous amplification and detection of the amplification products in a single reaction. As another alternative, the amplification products can be isolated and then contacted with molecular beacon probes comprising SEQ ID NOs: 6, 7, 8, and/or 9.

The term "label" as used herein means a molecule or moiety having a property or characteristic which can be detected. A label can be directly detectable, as with, for example, radioisotopes, fluorophores, chemiluminophores, enzymes, colloidal particles, fluorescent microparticles and the like; or a label may be indirectly detectable, as with, for example, specific binding members. Directly detectable labels may require additional components such as, for example, substrates, triggering reagents, light, and the like to enable detection of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

A molecular beacon probes as used herein comprises at least two moieties to form at least one label. A molecular beacon is a moiety comprising a first chemical moiety conjugated to a nucleic acid or nucleic acid analog that is conjugated to a second chemical moiety. (See, e.g., Tyagi et al., Nat. Biotechnol., 14, 303–308 (1996), and U.S. Pat. Nos. 5,119,801 and 5,312,728, each of which is incorporated by reference). The nucleic acid, or nucleic acid analog, is capable of binding to itself to form a stem-and-loop structure, which brings the first chemical moiety into close proximity to the second chemical moiety. When in close proximity, the first chemical moiety, or the second chemical moiety, or the combination of the chemical moieties either produce no detectable signal, or in the alternative produce an "unbound signal" that is characteristic of the molecular beacon when it is not bound to the target or amplification product. The first chemical moiety and second chemical moiety are each preferably located at opposite termini of the nucleic acid sequence, but can also be incorporated into internal positions within the nucleic acid.

Conversely, when the molecular beacon is contacted with the target or amplification product, the molecular beacon probe binds with the target and/or amplification product. Binding of the molecular beacon to the target or amplification product forces the molecular beacon into a conformation that separates the first chemical moiety and the second chemical moiety of the molecular beacon. In this separated state, the molecular beacon generates a "bound signal" that can be distinguished from the "unbound signal." The bound signal can be generated by the first chemical moiety, the second chemical moiety, by both moieties, or can be the absence of the unbound signal.

The first chemical moiety and the second chemical moiety can be any suitable atom or molecular moiety capable of detection. Preferred embodiments of the first chemical moiety and second chemical moiety of the molecular beacon probe include any suitable fluorophore. The first chemical moiety and second chemical moiety preferably are capable of interacting via Fluorescence Resonance Energy Transfer (FRET) or through collisional quenching.

FRET is a form of molecular energy transfer by which energy is passed between a donor molecule and an acceptor molecule. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance between a donor molecule, which is a fluorophore, and an acceptor molecule. The donor absorbs a photon and transfers energy nonradiatively to the acceptor (reviewed in Clegg, *Methods Enzymology*, 211, 353–388 (1992)).

Depending on what kind of fluorophore molecule is being monitored (i.e. a donor or an acceptor), the fluorescence is either quenched or enhanced by a transfer of energy. Resonant overlap of the excitation and emission spectra of two fluorophores enables an energy transfer. Energy transfer also depends on physical factors, such as the orientation and distance between the two fluorophores. Resonance energy transfer is well known in the art, and skilled workers are able to choose compatible pairs for fluorescence quenching or enhancement, along with useful excitation and fluorescence detection wavelengths. The disclosures of U.S. Pat. Nos. 5,691,146; 5,876,930; 5,723,591; 5,348,853; 5,119,801; 5,312,728; 5,962,233; 5,942,283; 5,866,336, discussing such fluorophores, are incorporated herein by reference.

Whether a fluorophore is a donor or an acceptor is defined by its excitation and emission spectra, and that of the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have excitation maximum at 514 nm).

Molecules that are commonly used in FRET include Fluorescein, 5-carboxyfluorescein (FAM), 2'7' dimethoxy-4'5'-dichloro-6-carboxyfluorescein (JOE), rhodamine, 6-carboxyrhodamine (R6G), N,N,N,N-tetramethyl-6-carboxyrhodamine (TAMRA), 6-carboxy-X-rhodamine (ROX), 4-(4'-dimethylaminophenylazo)benzoic acid (DABCYL), and 5-(2'-aminoethyl)aminonaphthalene-1-sulfonic acid (EDANS).

Non-FRET based molecular beacon probes, such as but not limited to collisional quenching pairs, are also preferred in the context of the present invention. Collisional quenching pairs are described in U.S. Pat. No. 6,150,097, which is hereby incorporated.

Other suitable labels are known in the art, and can readily be selected by the skilled artisan, irrespective of whether the label is to be used in FRET.

A "solid support", refers to any material which is insoluble, or can be made insoluble by a subsequent reaction. Thus, a solid support can be can be latex, plastic, derivatized plastic, magnetic or non-magnetic metal, glass, silicon or the like. A vast array of solid support configurations are also well known and include, but are not intended to be limited to, beads, shavings, grains, particles, plates, or tubes.

According to one embodiment, hybrids can be detected by incorporating labels in the primer and/or probe sequences to facilitate detection. Hence, first and second specific binding members attached to the primers and probes can be employed to immobilize the hybrids to, for example, microparticles and detect the presence of the hybrids on the microparticles with the assistance of a conjugate.

According to another embodiment, a combination of specific binding members and directly detectable labels can be employed to detect hybrids. For example, specific binding members can be introduced in the hybrids using primers labeled with specific binding members. A directly detectable label can be incorporated into the hybrids using a probe that has been labeled with a directly detectable label. Hence, hybrids can be immobilized to a microparticle using the specific binding member and directly detected by virtue of the label on the probe. It will be understood that other detection configurations are a matter of choice for those skilled in the art.

According to a preferred embodiment, "oligonucleotide hybridization PCR" (variably referred to herein as "OH PCR") amplification reaction as described in U.S. patent application Ser. No 08/514,704, filed Aug. 14, 1995, now abandoned, that is herein incorporated by reference, is employed to detect the target sequence. Briefly, the reagents employed in the preferred method comprise at least one amplification primer and at least one internal hybridization probe, as well amplification reagents for performing an amplification reaction. The primer sequence is employed to prime extension of a copy of a target sequence (or its complement) and is labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

According to the above preferred embodiment the probe initially is part of the reaction mixture, it is preferable to select primers, probes and amplification conditions such that the probe sequence has a lower melt temperature than the primer sequences so that upon placing the reaction mixture under amplification conditions copies of the target sequence or its complement are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid (for example 8 to 15 minutes) and particularly through the temperature range in which an enzyme having polymerase activity is active for primer extension. Such a rapid cooling favors copy sequence/probe hybridization rather that primer/copy sequence hybridization and extension.

The following examples further illustrate the present invention and are not intended to limit the invention in any way.

EXAMPLES

The following examples demonstrate detection of a single nucleotide polymorphism in the beta-2 adrenergic receptor gene using the DNA oligomer primers and probes herein provided. These DNA primers and probes are identified as SEQ ID NO. 2, SEQ ID NO. 3, SEQ ID NO. 4 and SEQ ID NO. 5, and as FAM and Dabcyl containing molecular beacon probes further comprising SEQ ID NO: 6, SEQ ID NO: 7, SEQ ID NO: 8 and SEQ ID NO: 9. A portion of a representative sequence from the beta-2 adrenergic receptor gene is designated herein as SEQ ID NO. 1.

In the following examples, SEQ ID NO. 2 and SEQ ID NO. 3 are used as amplification primers specific for a portion of both the wild type and mutant beta-2 adrenergic receptor gene. SEQ ID NO. 4 is an internal hybridization probe that detects the wild type allele of the beta-2 adrenergic receptor gene amplification product. SEQ ID NO. 5 is an internal hybridization probe that detects the variant (mutant) allele of the beta-2 adrenergic receptor gene amplification product. Similarly, SEQ ID NO: 6 and SEQ ID NO: 7 render molecular beacon probes specific for the wild type allele, while SEQ ID NO: 8 and SEQ ID NO: 9 render the molecular beacon probe specific for the variant form of the beta-2 adrenergic receptor gene or gene amplification product.

Example 1

Preparation of beta-2 Adrenergic Receptor Gene Primers and Probes

A. beta-2 Adrenergic Receptor Primers

Primers were designed to bind and allow amplification of the target sequence containing both wild type and variant (mutant) alleles of the beta-2 adrenergic receptor gene by oligonucleotide hybridization PCR. These primers were SEQ ID NO: 2 and SEQ ID NO: 3. Primer sequences were synthesized using standard oligonucleotide synthesis methodology. Additionally, SEQ ID NO. 3 was haptenated with carbazole at the 5'end using standard cyanoethyl phosphoramidite coupling chemistry as described in U.S. Pat. No. 5,424,414 incorporated herein by reference.

B. Wild Type and Mutant beta-2 Adrenergic Receptor Probes

Probes were designed to hybridize with the amplified target sequence of either the wild type or variant (mutant) allele in the beta-2 adrenergic receptor gene by oligonucleotide hybridization. These probes were SEQ ID NO. 4 for the wild type allele, and SEQ ID NO. 5 for the variant (mutant) allele. Probe sequences were synthesized using standard oligonucleotide synthesis methodology. SEQ ID NO. 4 was haptenated with an adamantane at the 5' end followed by 10 thymidines, and blocked with phosphate at the 3' end. SEQ ID NO. 5 was haptenated with a dansyl at the 5' end followed by 10 thymidines, and blocked with phosphate at the 3' end. All syntheses used standard cyanoethyl phosphoramidite coupling chemistry as described in U.S. Pat. No. 5,464,746 (herein incorporated by reference).

C. Wild Type and Mutant beta-2 Adrenergic Receptor Molecular Beacon Probes

Molecular beacon probes were designed to hybridize with the amplified target sequence of either the wild type or variant (mutant) allele in the beta-2 adrenergic receptor gene by oligonucleotide hybridization. These probes comprised the nucleotide sequences designated SEQ ID NO: 6 and SEQ ID NO: 7 for the wild type allele, and SEQ ID NO: 8 and SEQ ID NO: 9 for the variant allele. Probe sequences were synthesized on disposable pre-packed columns of controlled pore glass (CPG) with the 3' dabcyl attached using standard oligonucleotide synthesis methodology and terminated with FAM at the 5' end. All syntheses used standard cyanoethyl phosphoramidite coupling chemistry as described in U.S. Pat. No. 5,464,746 (herein incorporated by reference).

Example 2

Detection of beta-2 Adrenergic Receptor Polymorphism

A. General Procedure

DNA was extracted from whole blood using either the QIAamp® Blood Mini Kit (for samples less than or equal to 200 μl) or the QIAamp® Blood Maxi Kit (for sample volumes from 200 μl to 10 ml) (both kits from Qiagen, Valencia, Calif.) per the manufacturer's directions. The genotype of all samples was verified by sequencing. This allowed samples to be identified as either homozygous wild type, homozygous mutant or heterozygous at the beta-2 adrenergic receptor gene allele being tested for herein. In some cases, the purified DNA was quantitated by spectrophotometric absorbance of light at 260 nM.

DNA from the above samples was PCR amplified and detected using SEQ ID NO. 2 and SEQ ID NO. 3 primers with SEQ ID NO. 4 (wild type) and SEQ ID NO. 5 (mutant) probes as prepared in Example 1.

PCR was performed in 1×PCR buffer containing 50 mM N,N,-bis[2-Hydroxyethyl]glycine (Bicine), pH 8.1, 150 mM potassium acetate, 0.1 mM ethylene diamine-tetra-acetic acid, 0.02% sodium azide, 0.001% bovine serum albumin and 8% (w/v) glycerol. Recombinant *Thermus thermophilus* DNA polymerase was used at a concentration of 5 units/reaction, with dNTPs (dATP, dGTP, dTTP and dCTP) present at a final concentration of 150 μM each. SEQ ID NO. 2 and SEQ ID NO. 3 primers and the SEQ ID NO. 4 wild type probe were used at a concentration of 110 nM each, and the SEQ ID NO. 5 mutant probe was used at a concentration of 50 nM. A final concentration of 3.25 mM manganese chloride was also present in the reaction mixture. The total reaction volume was 0.2 ml, with a sample volume of 20 μl.

Reaction mixtures were amplified in an LCx® Thermal Cycler. Reaction mixtures were first incubated at 97° C. for 2 minutes, followed by 45 cycles of PCR amplification at 94° C. for 40 seconds, 55° C. for 40 seconds then 72° C. for 40 seconds. After the reaction mixtures were thermal cycled, the mixtures were maintained at 97° C. for 5 minutes and probe oligo hybridization was accomplished by rapidly lowering the temperature to 12° C. Samples were held at 12° C. for a minimum of 10 minutes, and thereafter until reaction products were analyzed and detected.

Reaction products were detected on the Abbott LCx® system (available from Abbott Laboratories, Abbott Park, Ill.). A suspension of anti-carbazole coated microparticles, an anti-adamantane antibody/alkaline phosphatase conjugate and an anti-dansyl antibody/β-galactosidase conjugate (available from Abbott Laboratories, Abbott Park, Ill.) were used in conjunction with the LC® to capture and detect the reaction products. The enzyme substrates used were 4-methyl-umbelliferyl phosphate (MUP) and 7-β-D-galactopyranosyloxy coumarin-4-acetic acid-(2-hydroxyethyl) amide (AUG) with the rate of conversion of substrate to product measured and reported as counts/second/second (c/s/s).

B. Target DNA Titration

DNA from each of the 3 genotypes (homozygous wild type, heterozygous and homozygous mutant), verified by sequencing, was isolated, quantitated and tested by the procedure above using varying amounts of DNA, from 25 ng per reaction to 500 ng per reaction, in the sample.

Data from this experiment is presented in TABLE 1 and shows that the wild type probe detected both the homozygous wild type and heterozygous beta-2 adrenergic receptor genotypes but did not detect the homozygous mutant beta-2 adrenergic receptor genotype as positive. The mutant probe detected both homozygous mutant and heterozygous beta-2 adrenergic receptor genotypes but did not detect the homozygous wild type beta-2 adrenergic receptor genotype as positive. As expected, both probes detected the heterozygous samples since they contain one wild type and one variant (mutant) allele. Additionally, the LCx reaction rate of the heterozygous samples was approximately half that of the homozygous samples, since the probe would have only one allele to react with rather than the 2 alleles present in the appropriate homozygous sample. Thus, all probes showed excellent specificity. All positive samples were detectable down to at least 25 ng of DNA per reaction.

TABLE 1

| beta-2 Adrenergic Receptor Genotype | 25 | 50 | 100 | 200 | 300 | 400 | 500 |
|---|---|---|---|---|---|---|---|
| | LCx ® rate (c/s/s) of Wild Type Probe DNA (ng) | | | | | | |
| Homozygous wild type | 747.3 | 794.8 | 819.2 | 931.4 | 924.8 | 882.0 | 831.5 |
| Heterozygous | 438.4 | 502.9 | 530.8 | 497.8 | 558.8 | 567.3 | 529.0 |
| Homozygous mutant | 52.5 | 51.9 | 56.5 | 55.9 | 62.8 | 82.4 | 66.7 |
| | LCx ® rate (c/s/s) of Mutant Probe DNA (ng) | | | | | | |
| Homozygous wild type | 46.9 | 48.7 | 87.4 | 59.6 | 53.2 | 54.9 | 54.2 |
| Heterozygous | 566.2 | 662.9 | 668.1 | 679.1 | 746.3 | 768.6 | 737.3 |
| Homozygous mutant | 964.8 | 1068.8 | 1105.9 | 1128.5 | 1209.9 | 1195.7 | 1206.4 |

C. Genotype Determination of Unknown Samples The procedure described in A. above was used to determine the beta-2 adrenergic receptor genotype of 20 samples. This result was then compared to that determined by sequencing.

As can be seen in TABLE 2, samples clearly reacted with only the wild type probe (homozygous wild type), only the mutant probe (homozygous mutant) or both probes (heterozygous). These results were verified by sequencing. Thus this method, using these primers and probes in the LCx format, is as accurate for determining the genotype at the beta-2 adrenergic receptor as sequencing, while being easier to perform.

TABLE 2

| Sample No. | Wild Type Probe LCx ® rate | Mutant Probe LCx ® rate | Genotype |
|---|---|---|---|
| 1 | 68.6 | 1115.5 | Homozygous mutant |
| 2 | 74.9 | 1118.1 | Homozygous mutant |
| 3 | 67.6 | 1109.2 | Homozygous mutant |
| 4 | 65.4 | 1118.0 | Homozygous mutant |

TABLE 2-continued

| Sample No. | Wild Type Probe LCx ® rate | Mutant Probe LCx ® rate | Genotype |
|---|---|---|---|
| 5 | 70.4 | 1173.7 | Homozygous mutant |
| 6 | 68.5 | 1061.3 | Homozygous mutant |
| 7 | 69.7 | 1061.6 | Homozygous mutant |
| 8 | 70.3 | 1083.7 | Homozygous mutant |
| 9 | 70.8 | 1194.2 | Homozygous mutant |
| 10 | 75.7 | 1163.6 | Homozygous mutant |
| 11 | 77.4 | 1166.2 | Homozygous mutant |
| 12 | 597.8 | 692.2 | Heterozygous |
| 13 | 564.6 | 675.0 | Heterozygous |
| 14 | 578.6 | 630.6 | Heterozygous |
| 15 | 637.5 | 677.1 | Heterozygous |
| 16 | 595.0 | 685.6 | Heterozygous |
| 17 | 594.1 | 663.1 | Heterozygous |
| 18 | 963.2 | 52.6 | Homozygous wild type |
| 19 | 878.6 | 51.6 | Homozygous wild type |
| 20 | 897.6 | 50.6 | Homozygous wild type |

Example 3

Detection of beta-2 Adrenergic Receptor Polymorphism with Molecular Beacon Probes Standard and unknown amplicons were prepared from 125 ng DNA isolated from whole blood by PCR reaction using 300 nM SEQ ID NO: 2 as the forward primer and 300 nM SEQ ID NO: 3 as the reverse primer. The polymerase chain reaction was carried out in 0.2 mL microAMP™ tubes from Perkin-Elmer in 50 μL total volume. The 1×PCR buffer comprised of 3 mM $MgCl_2$, dNTPs (200 μM final concentration), 0.025 U/μL (5 units) of AT Gold™, 60 nM ROX and 200 nM of a molecular beacon probe having a nucleic acid component designated SEQ ID NO: 6 or SEQ ID NO: 9 (It was found that molecular beacons comprising SEQ ID NOs: 6 and 9 performed better than those comprising SEQ ID NOs: 7 and 8. The reaction mixtures were first incubated at 95° C. for 10 minutes followed by 45 thermal cycles. Thermal cycles consisted of 94° C. melt for 30 seconds, 55° C. anneal and read data for 50 seconds, 72° C. extension for 30 seconds. PCR product was checked by agarose gel electrophoresis. Measurement of fluorescence data was performed on a 7700 ABI Sequence Detection System™ with reference dye ROX from PE Biosystems.

Each sample was subjected to three polymerase chain reactions. One of each triplicate was run with water instead of a molecular beacon probe; a second with a molecular beacon probe consisting of FAM—SEQ ID NO: 6—dabcyl; and a third with a molecular beacon probe consisting of FAM—SEQ ID NO: 9—dabcyl. The identity of standards and unknown samples were confirmed by the Sanger dideoxynucleotide sequencing method. Each sample homozygous for the wild type sequence gave strong fluorescence in the presence of the molecular beacon probe comprising SEQ ID NO: 6, and essentially no fluorescence when water or the molecular beacon probe comprising SEQ ID NO: 9 was substituted for the molecular beacon probe comprising SEQ ID NO: 6. Conversely, each sample homozygous for the variant sequence gave strong fluorescence in the presence of the molecular beacon probe comprising SEQ ID NO: 9, and essentially no fluorescence when water or the molecular beacon probe comprising SEQ ID NO: 6 was substituted for the molecular beacon probe comprising SEQ ID NO: 9. Similarly, in heterozygous samples, a medium-level of fluorescence was observed in reactions comprising either molecular beacon probe.

In all cases, fluorescence was detectable after about 28 or 30 cycles and was easily distinguishable from base line fluorescence by about 35 cycles.

While the invention has been described in detail and with reference to specific embodiments, it will be apparent to one skilled in the art that various changes and modifications may be made to such embodiments without departing from the spirit and scope of the invention.

What is claimed is:

1. A composition comprising a molecular beacon probe for detecting a target sequence, the molecular beacon probe comprising a label moiety and a nucleic acid having a nucleotide sequence selected from the group consisting of SEQ ID NO: 6, SEQ ID NO:7, SEQ ID NO: 8, and SEQ ID NO: 9.

2. The composition of claim 1, wherein the molecular beacon probe comprises a label moiety and a nucleic acid having a nucleotide sequence selected from the group consisting of SEQ ID NO: 6 and SEQ ID NO: 9.

3. The composition of claim 1, further comprising a nucleic acid having a nucleotide sequence selected from the group consisting of SEQ ID NO 2, and SEQ ID NO 3.

4. A method for detecting a target sequence in a test sample comprising the steps of:
(a) forming a reaction mixture comprising nucleic acid amplification reagents, a nucleic acid having the nucleotide sequence designated SEQ ID NO:2, a nucleic acid having the nucleotide sequence designated SEQ ID NO:3, and a test sample suspected of containing a target sequence;
(b) subjecting the mixture to amplification conditions to generate an amplification product;
(c) contacting the amplification product with a molecular beacon probe comprising a label moiety and a nucleic acid having a nucleotide sequence selected from the group consisting of SEQ ID NO: 6, SEQ ID NO:7, SEQ ID NO: 8 and SEQ ID NO: 9 such that in the presence of the target sequence the molecular beacon probe generates a signal; and
(d) detecting the signal generated by the beacon probe as an indication of the presence of the target sequence in the test sample.

5. The method of claim 4, wherein the molecular beacon probe therefore comprises a label moiety and a nucleic acid having a nucleotide sequence selected from the group consisting of SEQ ID NO: 6, and SEQ ID NO: 9.

6. A kit for amplifying a β2 adrenergic receptor target sequence comprising:
   (a) a nucleic acid having the nucleotide sequence of SEQ ID NO: 2 and a nucleic acid having the nucleotide sequence of SEQ ID NO: 3;
   (b) amplification reagents; and
   (c) a molecular beacon probe comprising a label moiety and a nucleic acid having a nucleotide sequence selected from the group consisting of SEQ ID NO: 6, SEQ ID NO: 7, SEQ ID NO: 8, and SEQ ID NO: 9.

7. The kit of claim 6, wherein the molecular beacon probe therefore comprises a label moiety and a nucleic acid having a nucleotide sequence selected from the group consisting of SEQ ID NO: 6 and SEQ ID NO: 9.

* * * * *

UNITED STATES PATENT AND TRADEMARK OFFICE
CERTIFICATE OF CORRECTION

PATENT NO. : 6,593,092 B2
DATED : July 15, 2003
INVENTOR(S) : Hong Yu et al.

It is certified that error appears in the above-identified patent and that said Letters Patent is hereby corrected as shown below:

<u>Column 16,</u>
Line 65, delete the word "therefore".

<u>Column 18,</u>
Line 4, delete the word "therefore".

Signed and Sealed this

Twenty-fourth Day of February, 2004

JON W. DUDAS
*Acting Director of the United States Patent and Trademark Office*

SEQUENCE LISTING

```
<160> NUMBER OF SEQ ID NOS: 9

<210> SEQ ID NO 1
<211> LENGTH: 106
<212> TYPE: DNA
<213> ORGANISM: Artificial Sequence
<220> FEATURE:
<223> OTHER INFORMATION: synthetic fragment

<400> SEQUENCE: 1
aacggcagcg ccttcttgct ggcacccaat agaagccatg cgccggacca cgacgtcacg      60
cagcaaaggg acgaggtgtg ggtggtgggc atgggcatcg tcatgt                    106

<210> SEQ ID NO 2
<211> LENGTH: 19
<212> TYPE: DNA
<213> ORGANISM: Artificial Sequence
<220> FEATURE:
<223> OTHER INFORMATION: synthetic fragments

<400> SEQUENCE: 2
aacggcagcg ccttcttgc                                                   19

<210> SEQ ID NO 3
<211> LENGTH: 19
<212> TYPE: DNA
<213> ORGANISM: Artificial Sequence
<220> FEATURE:
<223> OTHER INFORMATION: synthetic fragments

<400> SEQUENCE: 3
acatgacgat gcccatgcc                                                   19

<210> SEQ ID NO 4
<211> LENGTH: 15
<212> TYPE: DNA
<213> ORGANISM: Artificial Sequence
<220> FEATURE:
<223> OTHER INFORMATION: synthetic fragments

<400> SEQUENCE: 4
caatagaagc catgc                                                       15

<210> SEQ ID NO 5
<211> LENGTH: 13
<212> TYPE: DNA
<213> ORGANISM: Artificial Sequence
<220> FEATURE:
<223> OTHER INFORMATION: synthetic fragments
```

-continued

```
<400> SEQUENCE: 5
cccaatggaa gcc                                                              13

<210> SEQ ID NO 6
<211> LENGTH: 29
<212> TYPE: DNA
<213> ORGANISM: Artificial Sequence
<220> FEATURE:
<223> OTHER INFORMATION: synthetic fragments

<400> SEQUENCE: 6
cgtccgcacc caatagaagc catcggacg                                             29

<210> SEQ ID NO 7
<211> LENGTH: 29
<212> TYPE: DNA
<213> ORGANISM: Artificial Sequence
<220> FEATURE:
<223> OTHER INFORMATION: synthetic fragments

<400> SEQUENCE: 7
cgtccgatgg cttctattgg gtgcggacg                                             29

<210> SEQ ID NO 8
<211> LENGTH: 29
<212> TYPE: DNA
<213> ORGANISM: Artificial Sequence
<220> FEATURE:
<223> OTHER INFORMATION: synthetic fragments

<400> SEQUENCE: 8
cgtccgcacc caatggaagc catcggacg                                             29

<210> SEQ ID NO 9
<211> LENGTH: 29
<212> TYPE: DNA
<213> ORGANISM: Artificial Sequence
<220> FEATURE:
<223> OTHER INFORMATION: synthetic fragments

<400> SEQUENCE: 9
cgtccgatgg cttccattgg gtgcggacg                                             29
```